(12) United States Patent  
Nakamura

(10) Patent No.: US 7,477,458 B2  
(45) Date of Patent: Jan. 13, 2009

(54) ILLUMINATION OPTICAL SYSTEM

(75) Inventor: Minoru Nakamura, Hachioji (JP)

(73) Assignee: Olympus Corporation, Tokyo (JP)

( * ) Notice: Subject to any disclaimer, the term of this patent is extended or adjusted under 35 U.S.C. 154(b) by 360 days.

(21) Appl. No.: 11/178,291

(22) Filed: Jul. 12, 2005

(65) Prior Publication Data

US 2006/0122464 A1    Jun. 8, 2006

(30) Foreign Application Priority Data

Jul. 15, 2004    (JP)    ............... 2004-209013

(51) Int. Cl.  
*G02B 13/20* (2006.01)  
*G05D 25/00* (2006.01)

(52) U.S. Cl. ............... 359/707; 362/552; 362/558

(58) Field of Classification Search ............ 359/707; 362/552, 558

See application file for complete search history.

(56) References Cited

U.S. PATENT DOCUMENTS 5,961,197 A * 10/1999 Watai et al. ............ 362/628

6,710,923 B2 * 3/2004 Ito ............ 359/599  
2003/0214719 A1 * 11/2003 Bourdelais et al. ........ 359/599  
2004/0076396 A1 * 4/2004 Suga ............ 385/146

FOREIGN PATENT DOCUMENTS

JP    06-148519    5/1994  
JP    2000-193894    7/2000  
JP    2001-292956    10/2001

* cited by examiner

*Primary Examiner*—Jordan M. Schwartz  
(74) *Attorney, Agent, or Firm*—Kenyon & Kenyon LLP

(57) ABSTRACT

An illumination optical system for illuminating an object with light from a light source device comprises a plurality of optical surfaces. At least one of the optical surfaces is formed as a roughened surface and is arranged in a position other than closest to the object. Assuming that a total quantity of light emitted to the object by the illumination optical system is L, and a total quantity of light is $L_0$ emitted by a reference optical system in which all the roughened surfaces of the illumination optical system are replaced with polished surfaces, the illumination optical system satisfies the following condition:

$$0.70 \leq X \leq 0.95,$$

where $X = L/L_0$.

16 Claims, 14 Drawing Sheets

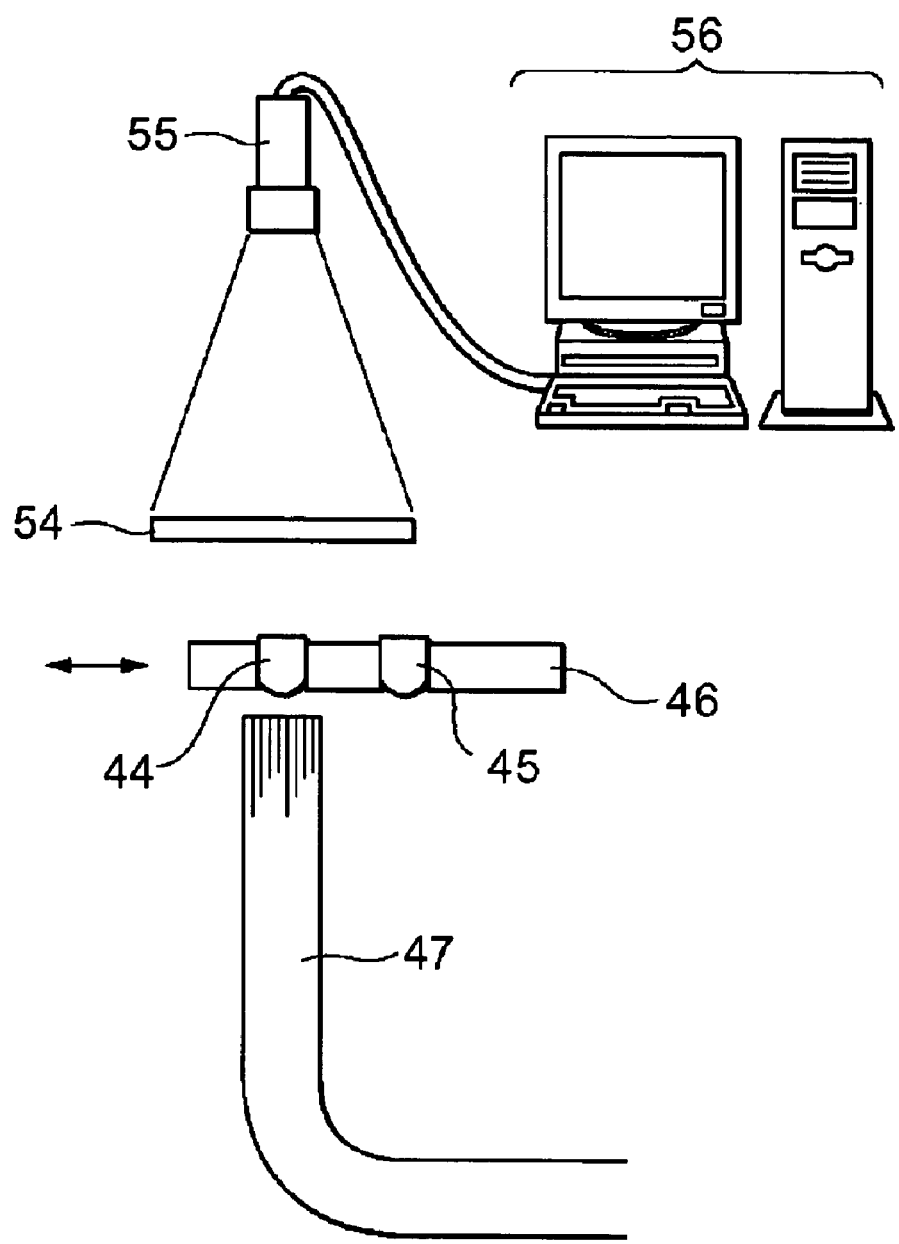

CORRELATION BETWEEN TOTAL LIGHT QUANTITY RATIO AND SURFACE ROUGHNESS (Ra)

CORRELATION BETWEEN LIGHT DISTRIBUTION UNEVENNESS RATIO AND SURFACE ROUGHNESS (Ra)

ILLUMINATION OPTICAL SYSTEM

CROSS REFERENCE TO RELATED APPLICATION

This application is based upon and claims the benefit of priority from Japanese Patent Application No. 2004-209,013, filed in Japan on Jul. 15, 2004; the contents of which are incorporated by reference.

BACKGROUND OF THE INVENTION

1. Field of the Invention

The present invention relates to an illumination optical system, particularly to an illumination optical system for use in an endoscope having a wide view field angle or a small diameter.

2. Description of the Related Art

An illumination optical system for an endoscope has been required to be capable of sufficiently brightly illuminating an observation object over a wide view field angle such as about 120° to 140° and to have no significant illumination unevenness. Moreover, in recent years, there has been a demand for observation in a wide range of a view field angle exceeding 140° so as to find more quickly a lesioned portion (in a case where a human body is observed) or a breakdown site (in a case where the inside of a machine is observed). On the other hand, there has been a demand for further reduction of the diameter of the insertion section of an endoscope in order to reduce the pain of a medical examinee and to observe a site having a smaller inner diameter in the body.

Here, illumination unevenness will be described in the illumination optical system for an endoscope. Illumination unevenness includes light distribution unevenness and color unevenness. The light distribution unevenness is generated because a light guide fiber bundle for transmitting illumination light from a light source to a tip end of an endoscope has a dot matrix form on its end surface. The color unevenness is caused by color dispersion of glass material of an illumination lens.

First, light distribution unevenness will be described. Usually, the light guide fiber bundle is made of a plurality of fine optical fibers each having a core C and a cladding CL that surrounds the core, and only the core part C transmits the light. Therefore, an emission end surface of the light guide fiber bundle emits the light in a dot matrix form as shown in FIG. 13A. As shown in FIG. 13B, light emitted from the emission end surface of the light guide fiber bundle 1 and passed through the illumination optical system ILO is projected onto an object surface 4. Therefore, as shown in FIG. 13C, the illumination light projected onto the object surface 4 causes the dot-matrix light distribution unevenness. Especially in an illumination optical system having a positive power, a conjugate surface with respect to the emission end surface of the light guide fiber bundle 1 comes closer to the object surface as compared with an illumination optical system having a negative power, and therefore the light distribution unevenness occurs more easily.

This dot-matrix light distribution unevenness can be blurred and made inconspicuous to a certain degree by adjusting the arrangement of the illumination optical system, the object to be illuminated, and the light guide fiber bundle 1. However, even in this case, radial light distribution unevenness still remains as shown in FIG. 14. In FIG. 14, a central part whose luminance is saturated is shielded so that a peripheral part is easily seen in which the light distribution unevenness occurs.

Next, color unevenness will be described. FIG. 15 is a schematic diagram showing a generated color unevenness in a case where the illumination optical system is composed of a positive lens. As shown in FIG. 15, since a light ray RY emitted from the light guide fiber bundle (not shown) is separated into colors by a prism function of the positive lens PL, a colored ring CR appears in the periphery of the illuminated area ILF. This is the color unevenness.

In view of the problem of illumination unevenness, an illumination optical system for an endoscope described in Laid-Open Japanese Patent Application No. 6-148519 has been devised.

FIGS. 16A and 16B show the illumination optical system described in Application No. 6-148519. The illumination optical system 6 shown in FIG. 16B includes three positive lenses. Two of them are composed of single fibers 5, 5 having large diameters, and claddings are formed on side surfaces of the lenses so that light is totally reflected by boundary surfaces between the lenses and the claddings. In this construction, the above-described light distribution unevenness is reduced, and a certain degree of wide illumination angle can be obtained.

The illumination optical system 6 shown in FIG. 16A comprises a plano-convex lens 2 whose surface on a light guide fiber bundle 1 side is formed into an aspherical surface, and a single fiber 5. In this illumination optical system, the number of optical components is reduced, the dot-matrix light distribution unevenness is prevented via the single fiber 5, the diameter is prevented from being thickened by the use of a lens having a positive power, and the colored ring is put outside the observation region via the aspherical surface to thereby prevent the color unevenness in an observation view field.

In the illumination optical system for the endoscope of Laid-Open Japanese Patent Application No. 2000-193894, as shown in FIG. 17, the system comprises a plano-convex lens 11 only, and a surface 11a on the light guide fiber bundle 1 side is formed into an aspherical and roughened surface having a light diffusion action. In this illumination optical system, the light distribution unevenness (dot-matrix and radial unevenness) and the color unevenness are prevented by the light diffusion action of the roughened surface. Since the illumination optical system comprises no single fiber, the total length thereof is shortened. Furthermore, by the use of the light diffusion action of the roughened surface, a wider illumination angle is achieved.

The illumination optical system for an endoscope is required to meet the following requirements: (1) total quantity of light for illuminating an object; (2) light distribution unevenness; and (3) light distribution profile. Among them, (1) the total quantity of light and (2) the light distribution unevenness are influenced by the state of the roughened surface which is a light diffusion surface.

Application No. 2000-193894 discloses that the roughened surface has a transmittance of 30% to 65%. The above (2) light distribution unevenness can be suppressed by the use of the roughened surface. However, 65% is insufficient as to (1) the total quantity of light. There has been a demand for an illumination optical system in which the elimination of the light distribution unevenness is compatible with the securing of the total quantity of light.

Another illumination optical system for the endoscope has been described in Laid-Open Japanese Patent Application No. 2001-292956.

FIG. 18 is an explanatory view showing a constitution of the illumination optical system for the endoscope described in Application No. 2001-292956, FIG. 18B is a front view, and FIG. 18A is a transverse sectional view. The illumination optical system ILO comprises a plano-concave lens L having a function of broadening the light distribution (illumination angle) and a square rod member IL. Patent Document 3 teaches that it is preferable to use the illumination optical system (L, IL) whose front surface is formed into a non-circular, elongated, and substantially rectangular shape or semicylindrical shape having an aspect ratio other than 1. Moreover, in this case, by the use of the roughened surface, the light distribution unevenness that tends to be caused in the short-side direction Y of the front surface is prevented. An objective optical system OBS that includes lenses OL1 and OL2 is arranged side by side with the illumination optical system in a hard tip end portion of the endoscope. CCD denotes a charge coupled device as an image sensor, LG denotes an image guide fiber bundle and CG denotes a cover glass arranged on the exit end surface of the image guide fiber bundle LG.

In the illumination optical system for the endoscope described in Application No. 2001-292956, the roughened surface is defined only by mesh size (#300 to #2000) of abrasive grains for use in a grinding step at the time of working of the roughened surface.

BRIEF SUMMARY OF THE INVENTION

According to one aspect of the present invention, there is provided an illumination optical system for illuminating an object with light from a light source device. The illumination optical system comprises a plurality of optical surfaces, at least one of which is formed as a roughened surface and is arranged in a position other than closest to the object. Assuming that a total quantity of light L is emitted to the object by the illumination optical system, and a total quantity of light $L_0$ is emitted by a reference optical system in which all the roughened surfaces of the illumination optical system are replaced with polished surfaces, the illumination optical system satisfies the following condition:

$$0.70 \leq X \leq 0.95,$$

where $X=L/L_0$.

According to another aspect of the present invention, there is provided an illumination optical system for illuminating an object with light from a light source device. The illumination optical system comprises a plurality of optical surfaces, at least one of which is formed as a roughened surface and is arranged in a position other than closest to the object. Assuming that an evaluated value of light distribution unevenness $\xi$ is projected to the object by the illumination optical system, and an evaluated value of light distribution unevenness $\xi_0$ is projected by a reference optical system in which all the roughened surfaces of the illumination optical system are replaced with polished surfaces, the illumination optical system satisfies the following condition:

$$0.30 \leq V \leq 0.70,$$

where $V=\xi/\xi_0$.

According to still another aspect of the present invention, there is provided an illumination optical system for illuminating an object with light from a light source device. The illumination optical system comprises a plurality of optical surfaces, at least one of which is formed as a roughened surface and is arranged in a position other than closest to the object. Assuming that a total quantity of light L is emitted to the object by the illumination optical system, a total quantity of light $L_0$ is emitted by a reference optical system in which all the roughened surfaces of the illumination optical system are replaced with polished surfaces, an evaluated value of light distribution unevenness $\xi$ is projected to the object by the illumination optical system, and an evaluated value of light distribution unevenness $\xi_0$ is projected by a reference optical system in which all the roughened surfaces of the illumination optical system are replaced with polished surfaces, the illumination optical system satisfies the following condition:

$$0.85 \leq X \leq 1.00, \text{ and}$$

$$0.60 \leq V \leq 0.95,$$

where $X=L/L_0$ and $V=\xi/\xi_0$.

Other features and advantages of the present invention will be clarified in the description of embodiments and appended claims.

BRIEF DESCRIPTION OF THE DRAWINGS

FIGS. 5A to 5B are explanatory views showing Embodiment 3 of the present invention, in which FIG. 5A is a sectional view along the optical axis and FIG. 5B is a front view of FIG. 5A viewed from the left side;

FIGS. 7A to 7B are explanatory views showing steps of manufacturing the plano-convex lens provided with the roughened surface, which is a component of Embodiments 1 and 2, in which FIG. 7A is an explanatory view of primary working, and FIG. 7B is an explanatory view of secondary working;

FIG. 9 is an explanatory view showing an apparatus for evaluation of light distribution unevenness of the plano-convex lens;

FIG. 10A to 10F are diagrams showing examples of images and a graph obtained when the light distribution unevenness of a lens having large light distribution unevenness is evaluated by using the apparatus shown in FIG. 9, in which FIG. 10A shows an image indicating actual light distribution unevenness, FIGS. 10B, 10E and 10F shows an image subjected to image processing in order to emphasize the light distribution unevenness, FIG. 10C shows an image whose coordinate is converted in order to facilitate quantitative evaluation of radial streaks of FIG. 10B, and FIG. 10D is a graph showing a result subjected to a two dimensional Fourier transform assuming that a size of the image of FIG. 10C is 1 in an abscissa direction;

FIGS. 13A to 13C are explanatory views showing the construction of a light guide fiber bundle, in which FIG. 13A is a perspective view showing an end surface of the light guide fiber bundle, FIG. 13B is a sectional view along an optical axis, showing a schematic constitution of a conventional illumination optical system provided with a light guide fiber, and FIG. 13C is an explanatory view of light distribution unevenness in the conventional illumination optical system shown in FIG. 13B;

FIGS. 18A to 18B are explanatory views showing the feature of still another conventional illumination optical system, in which FIG. 18A is a transverse sectional view, and FIG. 18B is a front view;

DETAILED DESCRIPTION

Figure 1:
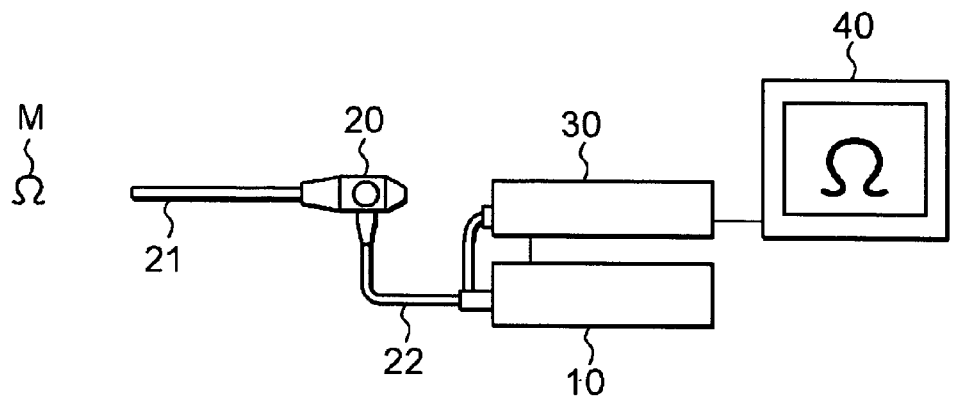
FIG. 1 is a schematic diagram showing one example of an endoscope system to which an illumination optical system of the present invention is applicable.

In this specification, surface roughness of an optical surface is defined by "JIS B 0601:2001 (ISO 4287:1997)", and the roughness is calculated assuming that a reference length lr (equal to a cutoff value λc) is 0.08 mm for obtaining a defined roughness curve. A defined "arithmetic average roughness" Ra is given by the following equation. Here, Z (x) denotes an ordinate value, and the value indicates a height of the roughness curve in a position x.

$$Ra = \frac{1}{lr}\int_0^{lr} |Z(x)| dx$$

Moreover, a "roughened surface" is distinguished from a "polished surface" based on the arithmetic average roughness Ra which is a measure of surface roughness. That is, in this specification, a polished surface satisfies the inequality of Ra<0.005 μm, and a roughened surface satisfies Ra≧0.005 μm.

In one aspect, the illumination optical system of the present invention is used for illuminating an object with light from a light source device. The illumination optical system comprises a plurality of optical surfaces, at least one of which is formed as a roughened surface and is arranged in a position other than closest to the object among optical surfaces included in the illumination optical system. In the illumination optical system, assuming that a total quantity of light L is emitted to the object by the illumination optical system, and a total quantity of light $L_0$ is emitted by a reference optical system in which all the roughened surfaces of the illumination optical system are replaced with polished surfaces, a total light quantity ratio X ($X=L/L_0$) preferably satisfies the following condition (1):

$$0.70 \leq X \leq 0.95 \tag{1}$$

When the condition (1) is satisfied, it is possible to minimize the light quantity loss caused by the roughened surface used in order to suppress light distribution unevenness. It is also possible to suppress fluctuation of the total emitted light quantity by a manufacturing error of the roughened surface, which is difficult to manage.

Further, it is more preferable to satisfy the following condition (1'):

$$0.78 \leq X \leq 0.92 \tag{1'}$$

In another aspect, the illumination optical system of the present invention is used for illuminating an object with light from a light source device. The illumination optical system comprises a plurality of optical surfaces, at least one of which is formed as a roughened surface and is arranged in a position other than closest to the object among optical surfaces included in the illumination optical system. In the illumination optical system, assuming that an evaluated value of light distribution unevenness ξ is projected to the object by the illumination optical system, and an evaluated value of light distribution unevenness $ξ_0$ is projected by a reference optical system in which all the roughened surfaces of the illumination optical system are replaced with polished surfaces, a light distribution unevenness ratio V ($V=ξ/ξ_0$) preferably satisfies the following condition (2):

$$0.30 \leq V \leq 0.70 \tag{2}$$

When the condition (2) is satisfied, the light distribution unevenness will become small enough to obtain high quality images. Further, it is more preferable to satisfy the following condition (2'):

$$0.35 \leq V \leq 0.60 \tag{2'}$$

It is more preferable if the illumination optical system satisfies both the conditions (1) and (2). In this case, the required performance can be obtained sufficiently and efficiently.

The illumination optical system preferably is composed of one positive lens. In this arrangement, an illumination optical system whose outer diameter and total length are small and whose manufacturing costs are small is obtained.

The illumination optical system preferably comprises one positive lens and a single fiber as viewed from an object side. In this construction, since the single fiber has the effect of reducing the light distribution unevenness, it is possible to weaken the diffusive function of the roughened surface and to reduce the light quantity loss in the roughened surface, and a brighter illumination optical system is obtained.

The illumination optical system of the present invention preferably satisfies the following condition (3):

$$\sqrt{Sx}/dr < 1 \tag{3}$$

where dr denotes the length of the single fiber in the optical axis direction and Sx denotes the maximum value of an area of a section of an optical member forming the illumination optical system, the section being vertical to an optical axis.

The value $\sqrt{Sx}/dr$ in the condition (3) has almost the same meaning as the numerical aperture (NA) of an illumination light flux, and provides a measure of occurrence of light distribution unevenness. When the condition (3) is not satisfied, the outer shape of the illumination optical system will become too large for the amount of light supplied therefrom.

It is more preferable that the illumination optical system satisfies the following condition (4):

$$-2 < \sqrt{Sx} \times \Phi 1 < 2 \quad (4),$$

where Sx denotes a maximum value of an area of a section of an optical member forming the illumination optical system, the section being vertical to an optical axis, and $\Phi 1$ denotes an optical power of the illumination optical system.

The value $\sqrt{Sx} \times \Phi 1$ in the condition (4) has almost the same meaning as the numerical aperture (NA) of an illumination light flux, and constitutes a measure of occurrence of light distribution unevenness in the same manner as the above condition (3). When the condition (4) is not satisfied, the outer shape of the illumination optical system will become too large for the amount of light supplied therefrom.

Additionally, the illumination optical system preferably includes at least one optical member whose sectional shape is not circular. There is a restriction as to the space in which the illumination optical system is disposed, and the space for arranging the illumination optical system is limited to a narrow range especially in an optical apparatus such as an endoscope. An illumination optical system that includes the optical member whose sectional shape is not circular, is advantageous for arrangement in the narrow space. When the outer shape of the optical member is formed into a shape other than a circular shape, the light distribution unevenness is easily generated. However, when the illumination optical system satisfies the above-described requirements, the light distribution unevenness can be prevented.

In the meantime, there are endoscopes in which a small sized image pickup device is used in order to reduce the diameter of the insertion section thereof. When using this type of endoscopes, the electronic images displayed on the observation monitor have less light distribution unevenness than the optical images. Therefore, the illumination optical system that satisfies the following conditions (5) and (6) provides, when used as an illumination optical system for the endoscopes of the above-mentioned type, an bright illumination in which the light distribution unevenness is suppressed to the level that does not cause any practical problems and also the variation of the total amount of light due to the manufacturing error of the roughened surface, which is difficult to be managed, is suppressed to the level that does not cause any practical problems. Where $X=L/L_0$ and $V=\xi/\xi_0$.

$$0.85 \leq X \leq 1.00 \quad (5)$$

$$0.60 \leq V \leq 0.95 \quad (6)$$

Figure 2:
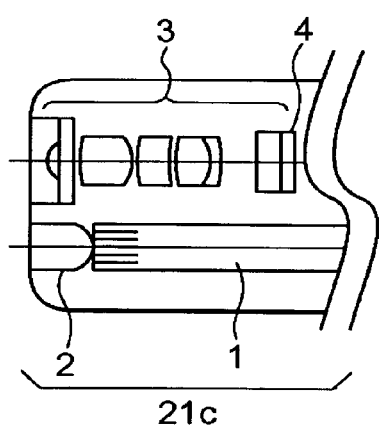
FIG. 2 is an explanatory view showing one example of a tip portion of the endoscope provided with the illumination optical system of the present invention.

FIG. 1 is a schematic diagram showing one example of an endoscope system to which the illumination optical system of the present invention can be applied. In FIG. 1, reference numeral 20 denotes an operating section of an endoscope, and 21 is an insertion section of the endoscope inserted into a body cavity or the like. Reference numeral 22 denotes a universal cord. The inside of the universal cord 22 is provided with a light guide fiber bundle that transmits light from a light source device 10. A hard tip section is disposed on a tip end of the insertion section 21. The reference numeral 30 denotes an image processor and 40 denotes a monitor for observing the image captured by the endoscope. M denotes an observation object. As shown in FIG. 2, a hard tip section 21c contains a tip portion of a light guide fiber bundle 1, an illumination optical system 2 and an objective optical system 3 including an image pickup element 4 that acquires an image of an observation object.

EMBODIMENT 1

Figure 3:
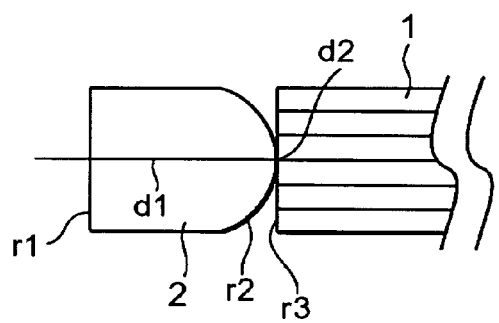
FIG. 3 is a sectional view along an optical axis, showing Embodiment 1 of the present invention.

FIG. 3 is a sectional view along an optical axis, showing a basic constitution of Embodiment 1 of the present invention. This illumination optical system comprises a plano-convex lens 2 having a positive power and disposed on an emission side (object side) of a light guide fiber bundle 1 which guides light from a light source device (not shown). A roughened surface is formed on a convex surface $r_2$ which is a second surface counted from the object side of the illumination optical system 2.

Here, a method will be described in which a lens in this embodiment is worked.

Figure 19:
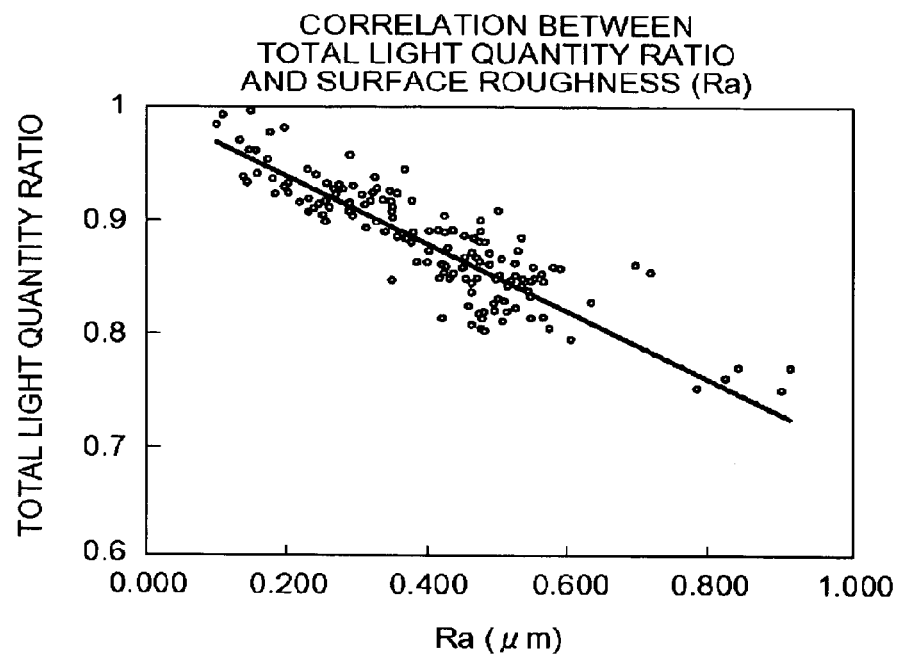
FIG. 19 is a graph showing the relation between an arithmetic average roughness (Ra) of a roughened surface included in the illumination optical system, measured by a probe type roughness measuring apparatus, and a total light quantity ratio.
Figure 20:
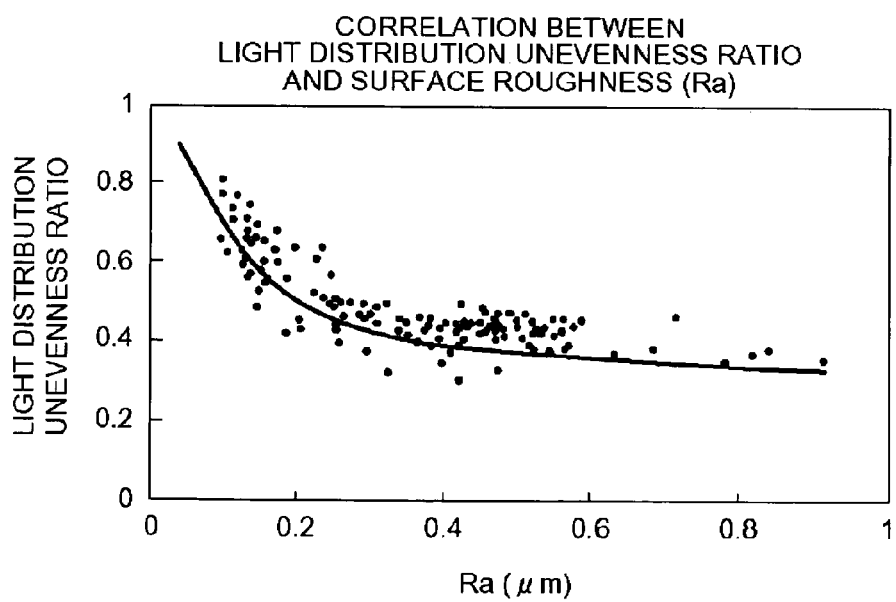
FIG. 20 is a graph showing the relation between the arithmetic average roughness (Ra) of the roughened surface included in the illumination optical system, measured by the probe type roughness measuring apparatus, and a light distribution unevenness ratio.

FIGS. 19 and 20 show the relation between an arithmetic average roughness (Ra) measured by a probe type roughness measuring apparatus and a total light quantity ratio, and the relation between the arithmetic average roughness (Ra) measured by the probe type roughness measuring apparatus and a light distribution unevenness ratio, respectively. As shown in FIGS. 19 and 20, from a broader view, the total light quantity ratio and the light distribution unevenness ratio have correlations with the surface roughness (Ra). However, in detail, a fluctuation of about 5 to 8% is generated in both the light quantity ratio and the light distribution unevenness ratio for equal surface roughness (Ra). In the method described hereinafter, the fluctuation can be reduced.

Figure 6:
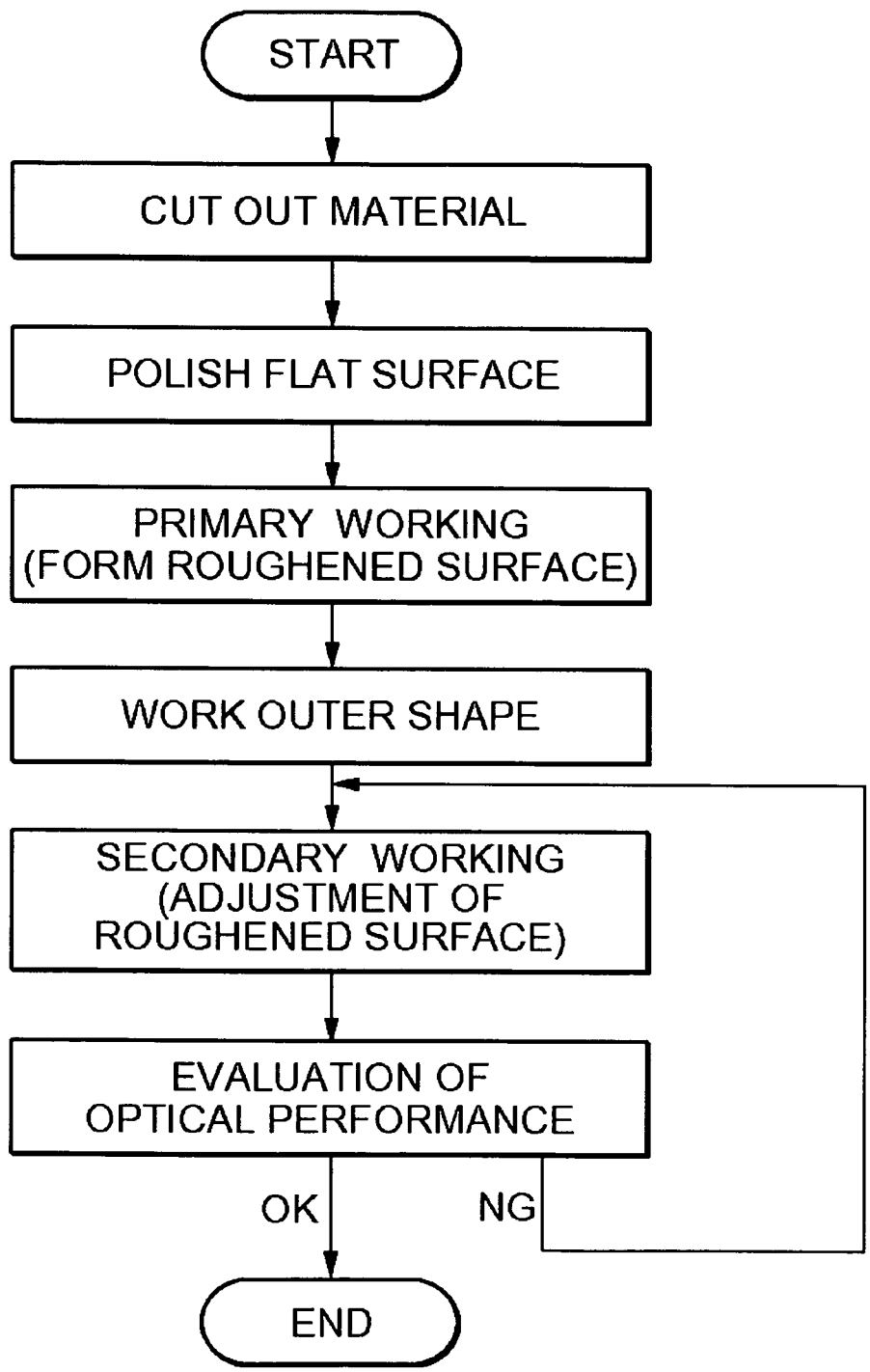
FIG. 6 is a flowchart showing steps of manufacturing a plano-convex lens provided with a roughened surface, which is a component of Embodiments 1 and 2.

FIG. 6 is a flowchart showing steps of manufacturing a plano-convex lens provided with a roughened surface for use in the illumination optical system.

Figure 7A:
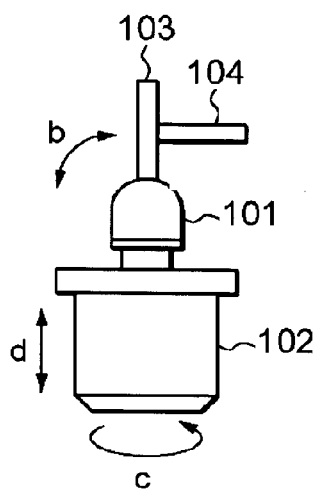

First, glass material is cut out into an appropriate size, and a flat surface is polished. The polished glass 101 is bonded and fixed to a lens polishing jig 102 with a flat-face side disposed downwards as shown in FIG. 7A.

Next, the process enters a step of forming a roughened surface on a convex aspherical surface as primary working. FIG. 7A is an explanatory view showing a state of the primary working. The lens polishing jig 102 and the material 101 rotate in a direction shown by an arrow c centering on a central axis of the jig. A grindstone 103 revolves around a material surface in an arrow b direction while rotating centering on a rotation axis 104. Moreover, the lens polishing jig 102 moves in an arrow d direction (vertical direction in the figure). Accordingly, the roughened surface and the convex aspherical surface are simultaneously formed. A computer controls the directions, amounts, and speeds of the rotations and/or the movements of the lens polishing jig 102, material 101, and grindstone 103. The computer has been set to optimum conditions determined before the working. Moreover, abrasive grains of the grindstone are similarly set for optimum conditions. An outer shape of the lens is formed by this working apparatus after forming the roughened surface.

Figure 7B:
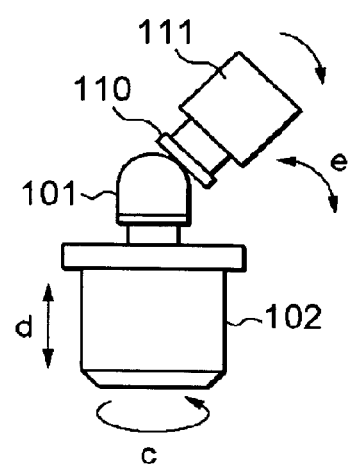

Next, the process enters a step of adjusting the roughened surface as a secondary working. FIG. 7B is an explanatory view showing a state of the secondary working. Unlike the primary working, in the secondary working, a polishing sheet 110 is used for working the material instead of the grindstone. The polishing sheet 110 is made by attaching a sheet mixed with a polishing material on the surface of a sponge sheet. The working jig 111 equipped with this polishing sheet 110 is revolved in the direction of an arrow e, and the lens polishing jig 102 is rotated in the direction of an arrow c in the same manner as in the primary working. Accordingly, a roughened state is adjusted in such a manner as to obtain a desired optical performance. Needless to say, these working conditions are set to optimum conditions determined beforehand. In this case, as a condition of the secondary working, a polishing sheet is used which polishes the roughened surface more smoothly.

Next, the prepared lens is removed from the lens polishing jig 102 to evaluate optical performance. The evaluation method and apparatus of the optical performance will be described later. When evaluation results fall within a desired range, the formation of the roughened surface is ended. When the results are not within the desired optical performance range, the secondary working is performed again, and adjustment is performed in such a manner as to achieve the desired optical performance. In the secondary working, the above-described polishing sheet is used when polishing the roughened surface more smoothly to achieve the optical performance. Conversely, to make the roughened surface coarse, a polishing sheet having coarse abrasive grains is used.

When the optical performance of the optical member itself constituting the illumination optical system is directly evaluated in this manner, it is possible to supply an illumination lens having the roughened surface stably and inexpensively with a reduced manufacturing error.

Next, the method and apparatus for evaluating optical performance will be described for use in the above-described working steps.

First, the evaluation method and apparatus will be described with respect to a total light quantity. The total light quantity relates to all luminous flux emitted to an object from the illumination optical system. The nature of luminous flux is well known as described in pages 325, 326 of "Latest Optical Technique, Handbook, issued by Asakura Shoten, the first printing of the first edition". A general measurement method is also described in pages 332, 334 of the same book. The general measurement method includes a goniophotometric method in which a light distribution of the emitted light is measured, integrated, and an integrating photometer method in which an integrating sphere is used.

Figure 8:
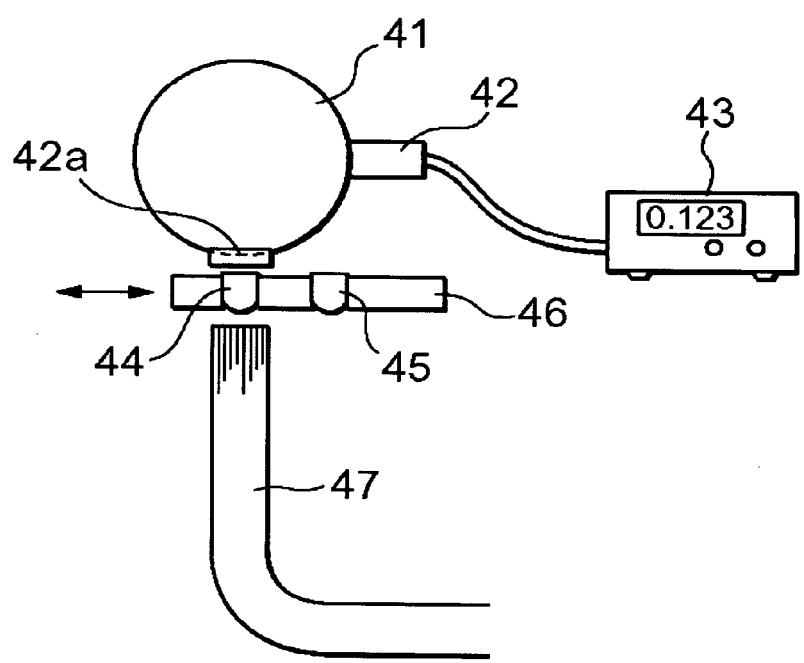
FIG. 8 is an explanatory view showing an apparatus for evaluation of a total quantity of light of the plano-convex lens.

FIG. 8 is an explanatory view showing an apparatus for evaluating the total quantity of light of the optical member constituting the illumination optical system. The evaluation apparatus of FIG. 8 is based on the integrating photometer method. This method measures the total quantity of emitted light of a reference optical system in which the roughened surface is replaced with a polished surface that is a usual lens surface, and the total quantity of emitted light of the lens having the roughened surface, and the ratio of these quantities is evaluated. In FIG. 8, reference numeral 41 denotes an integrating sphere which takes in the light emitted from the lens, 42 denotes a photosensor which measures the light quantity in the integrating sphere 41, and 43 denotes a controller section which calculates and displays a value from the photosensor 42 as a light quantity value. These components 41, 42 and 43 constitute an integrating sphere photometer. Reference numeral 44 denotes a plano-convex lens having a roughened surface which is an evaluation object, and 45 denotes a plano-convex lens which is used as a reference in which the roughened surface is replaced with a polished surface. Reference numeral 47 denotes a light guide fiber bundle formed of fibers which are the same in material, thickness and the like, as the fibers for use in the endoscope. The other end of the bundle is connected to a light source (not shown). The light guide fiber bundle 47 is fixed to an incident port 42a of the integrating sphere 47, such that the axis of the light guide fiber bundle 47 is coaxial with that of an incidence port 42a of the integrating sphere 41. The lenses 44 and 45 are disposed in a pallet 46. The pallet 46 is movable in the horizontal direction, and forms a switching mechanism. Accordingly, to measure the total light quantity of the reference lens 45, the pallet is slid in such a manner that the optical axis of the reference lens 45 is positioned on the axis of the light guide fiber bundle 47. To measure the total light quantity of the evaluation object lens 44, the pallet is slid in such a manner that the optical axis of the evaluation object lens 44 is positioned on the axis of the light guide fiber bundle 47. By the switching of this pallet 46, the desired quantities are obtained: a total light quantity $L_0$ of the reference lens 45; and a total light quantity L of the evaluation object lens 44, and a total light quantity ratio X $(=L/L_0)$ is calculated.

It is to be noted that the reference lens (or the reference optical system) is a lens (optical system) in which all the roughened surfaces are replaced with polished surfaces. Additionally, when the roughened surface is an aspherical surface, the aspherical surface may be replaced with a polished surface as such. However, in the reference lens (or the reference optical system), the surface may be replaced with a polished surface having a spherical shape whose mean square error is minimum with respect to the aspherical surface or a shape close to such spherical shape. The surface obtained by the replacing of the roughened surface with the polished surface is not subjected to anti-reflection coating.

Next, an evaluation method and apparatus will be described with respect to light distribution unevenness. FIG. 9 is an explanatory view showing the apparatus for evaluating the light distribution unevenness of the optical member constituting the illumination optical system. In the evaluation method of the light distribution unevenness, an evaluated value ξ of the light distribution unevenness of a lens having the roughened surface, and a evaluated value $ξ_0$ of the light distribution unevenness of a reference lens in which all the roughened surfaces are replaced with a polished surface, are measured and then the ratio of these values is evaluated.

In FIG. 9, reference numeral 44 denotes a plano-convex lens having the roughened surface which is an evaluation object, and 45 denotes a plano-convex lens which is used as a reference in which the roughened surfaces are replaced with the polished surfaces. Reference numeral 47 denotes a light guide fiber bundle formed of fibers which are the same in material, thickness and the like, as the fibers for use in the endoscope. The other end of the bundle is connected to a light source (not shown). The lenses 44, 45 are disposed on a pallet 46. The pallet 46 is movable in a horizontal direction, and forms a switching mechanism. Accordingly, to measure a light distribution unevenness amount of the reference lens 45, the pallet is slid in such a manner that the optical axis of the reference lens 45 is positioned on the axis of the light guide fiber bundle 47. To measure the light distribution unevenness amount of the evaluation object lens 44, the pallet is slid in such a manner that the optical axis of the evaluation object lens 44 is positioned on the axis of the light guide fiber bundle 47. Reference numeral 54 is a translucent screen on which a light distribution image is projected through the lens 44 (evaluation object). Reference numeral 55 denotes an electronic camera which takes a picture of the light distribution image projected on the screen 54 from the backside of the screen. Reference numeral 56 denotes a personal computer provided with an image processing board for analyzing the level of the light distribution unevenness from the light distribution image taken by the electronic image pickup camera 55. The computer is provided with software for analyzing the light distribution unevenness.

Figure 10A:
Figure 10B:
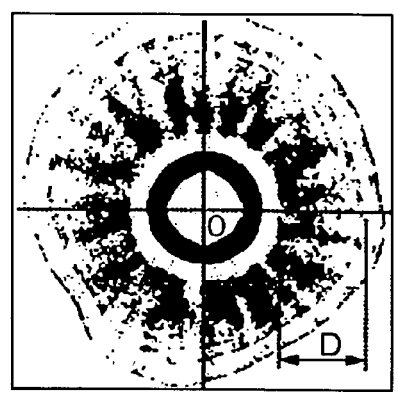
Figure 10C:
Figure 10D:
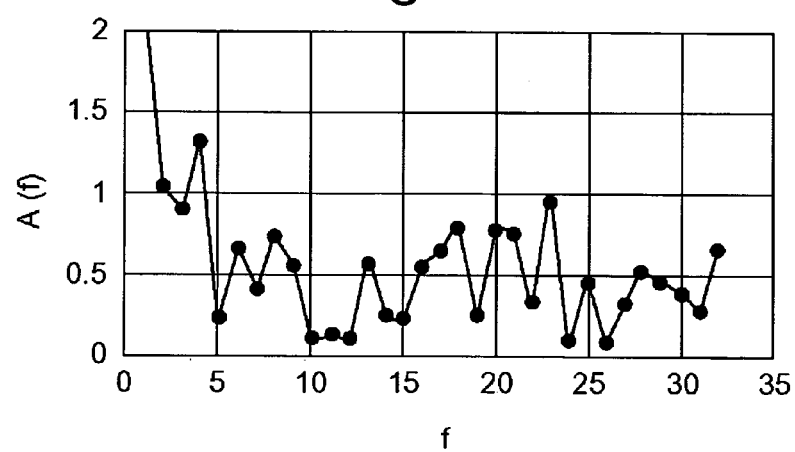

FIG. 10A to 10F are diagrams showing examples of images and a graph obtained when the light distribution unevenness of a lens having large light distribution unevenness is evaluated by using the apparatus shown in FIG. 9 and show the process how the image of the light distribution unevenness is analyzed. FIG. 10A shows an image indicating actual light distribution unevenness. In FIG. 10A, the central part whose luminance is saturated is shielded in order that a peripheral part in which the light distribution unevenness occurs is easily seen. FIG. 10B shows an image obtained through image processing in order to emphasize the unevenness of the actual image. In the image processing, a method that is referred to as local threshold binarization is used, and an edge smoothing is applied. The local threshold binarization is a method in which a threshold value for binarization of an image is determined by an average value of the output from the pixels arranged around the pixel to be binarized. In this example, the threshold value is determined by averaging of the output from the pixels arranged in a rectangular region centering on the pixel to be binarized, each side of which has 41 pixels. Then, the coordinate transformation is applied in order to facilitate quantitative evaluation of radial streaks of FIG. 10B. FIG. 10C shows an image subjected to the coordinate transformation. The coordinate transformation is conducted, assuming an angle of a polar coordinate as the abscissa, and a radial direction of the polar coordinate as the ordinate. In FIG. 10B, an origin is the point O, and a range to be converted is an annular zone having a width of D. When the light distribution unevenness is evaluated by using the Fourier transform, a two dimensional Fourier transform of the image of FIG. 10C is performed and an amplitude intensity distribution in a transverse-axis direction is used for the evaluated value $\xi$. FIG. 10D is a graph showing the result subjected to the two dimensional Fourier transform assuming that the size of the image of FIG. 10C is 1 in an abscissa direction. The ordinate indicates an amplitude intensity A, and the abscissa indicates a frequency f. The evaluated value $\xi$ is a sum of values of the amplitude intensity A (f) that is taken every one frequency increment from frequencies 5 to 30. That is, the following equation (I) results.

$$\xi = \sum_{f=5}^{30} A(f) \tag{I}$$

When the texture analysis is used for evaluating the light distribution unevenness, the evaluated value $\xi$ (and also the evaluated value $\xi_0$ of the reference optical system) is obtained through the texture analysis of the unevenness-emphasized image shown in FIG. 10B. The texture analysis means the texture feature extraction described in pages 517-523 of "Handbook of Image Analysis, edited by Mikio Takagi et al., issued by University of Tokyo Press, the first edition dated Jan. 17, 1991". The texture means the status in which fine patterns are uniformly distributed. The calculation method of statistical texture feature includes the first order statistics, the second order statistics and a higher order statistics. Here, the simultaneous occurrence matrix in the second order statistics is used for calculating the contrast of the image in order to quantify the light distribution unevenness. In fact, the simultaneous occurrence matrices are obtained in four pixel directions of 0 degree, 45 degrees, 90 degrees and 135 degrees in the unevenness-emphasized image shown in FIG. 10B assuming that the parameter of the matrices, that is, the interval of pixels, equals to 8. The evaluated value $\xi$ is obtained by averaging the contrast values calculated from respective simultaneous occurrence matrices.

Figure 11:
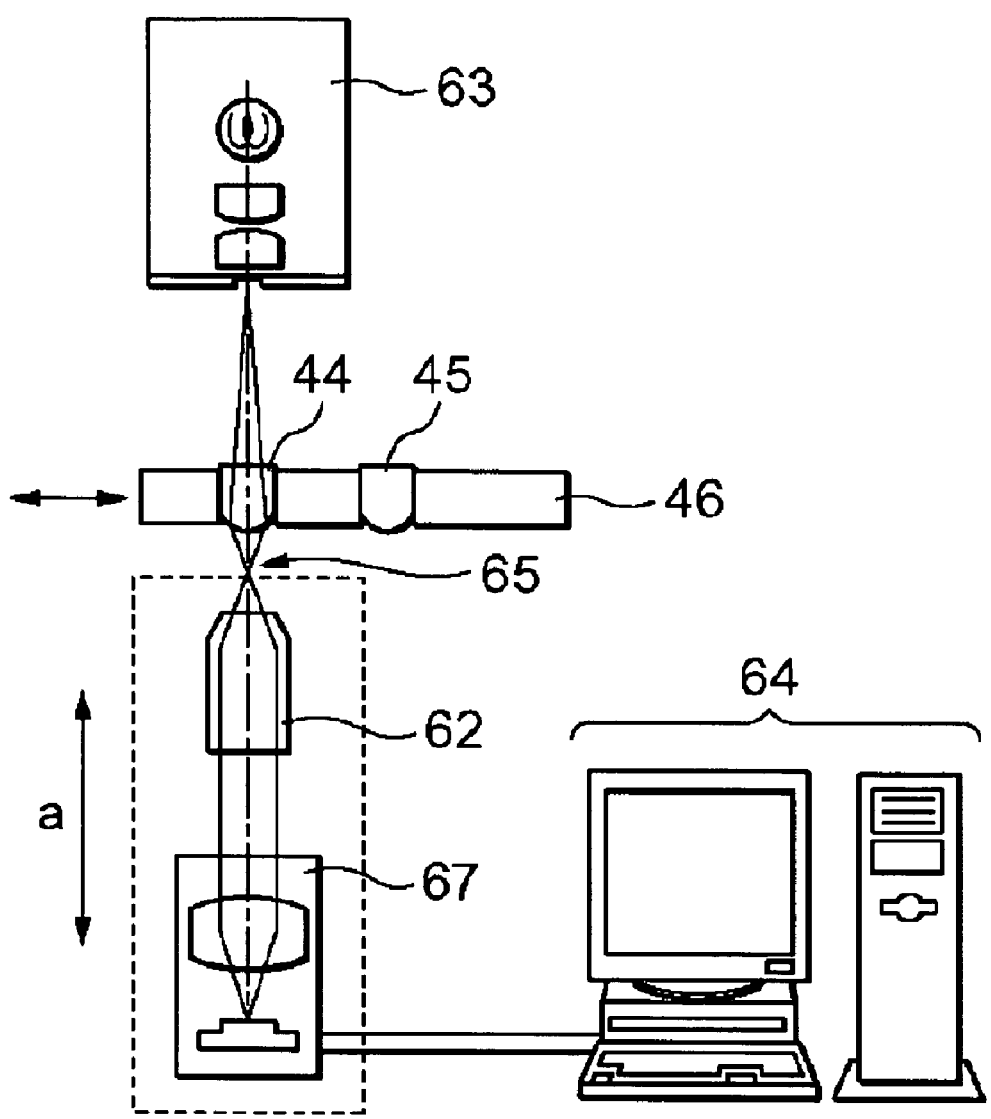
FIG. 11 is an explanatory view showing an evaluation apparatus for evaluating light distribution unevenness of the plano-convex lens by measuring a modulation transfer function (MTF)

As another mode of an evaluation method of light distribution unevenness, a method is usable in which a diffusion degree by the roughened surface of the evaluation object lens is represented by an MTF value indicating a blurred degree of a pinhole image, and this value is used as the evaluated value $\xi$ of the light distribution unevenness. A measurement apparatus for the light distribution unevenness in which the MTF is used will be described with reference to FIG. 11. In FIG. 11, reference numeral 44 denotes a plano-convex lens having the roughened surface (evaluation object), and 45 denotes a plano-convex lens which is used as a reference in which the roughened surface is replaced with the polished surface. The lenses 44 and 45 are disposed on a pallet 46. The pallet 46 moves in a horizontal direction to switch a measurement object. Reference numeral 62 denotes a microscope objective lens. Reference numeral 63 denotes a pinhole light source having a diameter of about 20 microns. Reference numeral 67 denotes an image forming optical system comprising an electronic image pickup element. In this example, since the evaluation object lens is a plano-convex lens, the pinhole image is formed as a blurred image whose best image plane is in the vicinity of the position 65. This image is focused on the image pickup element via the microscope objective lens 62 and the image forming optical system 67. The taken image is subjected to Fourier-transform using a personal computer 64 provided with an image processing board, and the MTF is obtained via software for calculating the MTF value of the evaluation object lens. The microscope objective lens 62 and the image forming optical system 67 are formed in such a manner as to be movable by control of the personal computer 64 in the direction of the arrow in FIG. 11 in order to search for the best image position.

Figure 12:
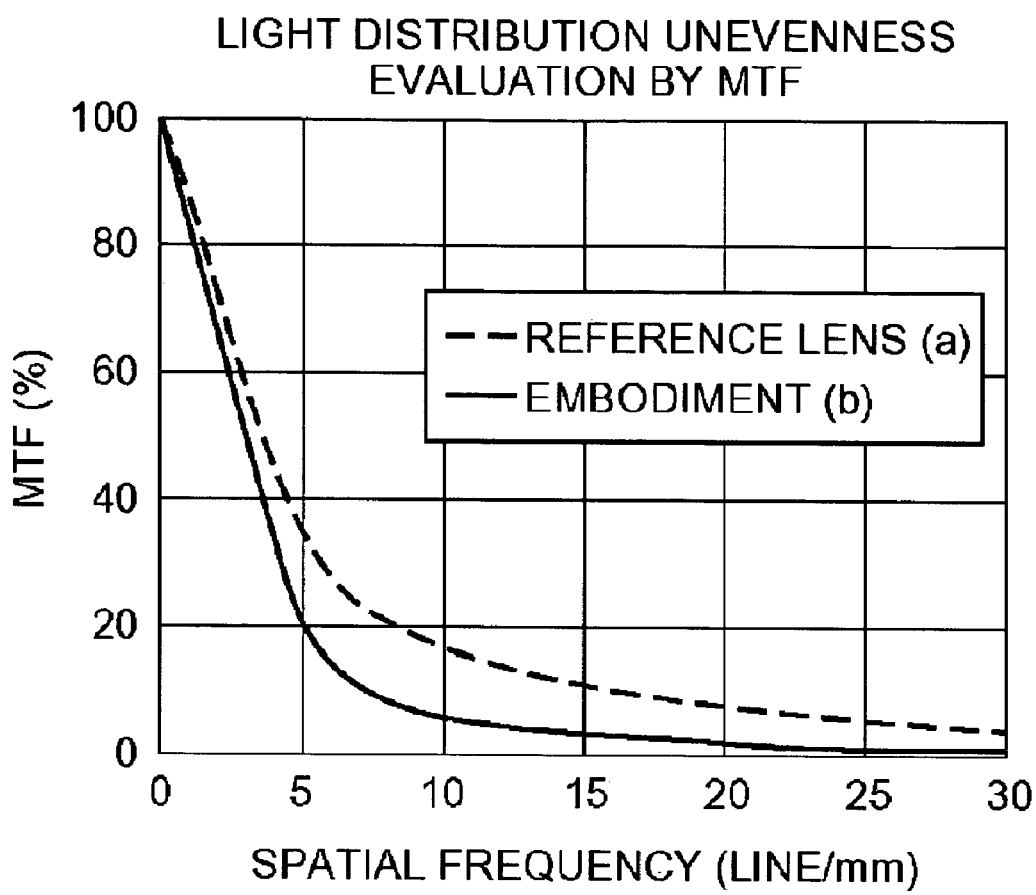
FIG. 12 is a graph showing results of measured MTFs of the plano-convex lens and a reference lens using the apparatus of FIG. 11.
Figure 13A:
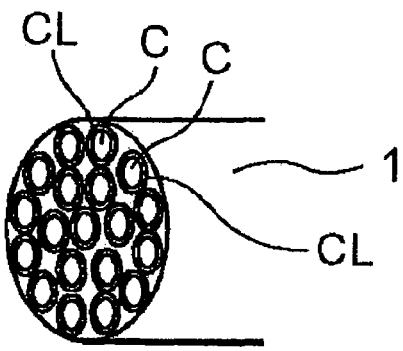
Figure 13B:
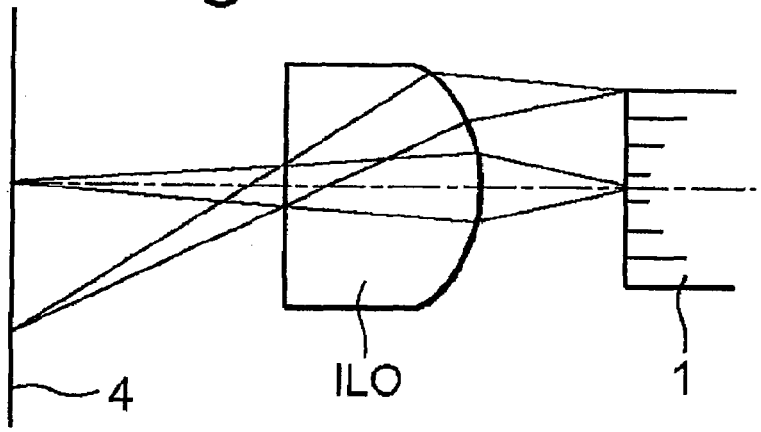
Figure 13C:
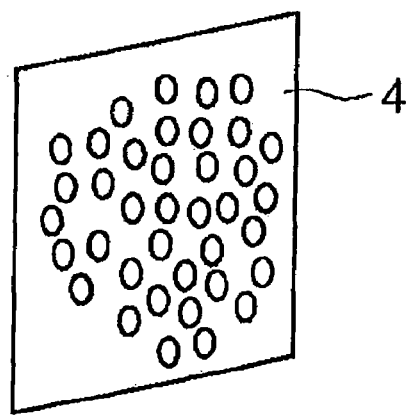
Figure 14:
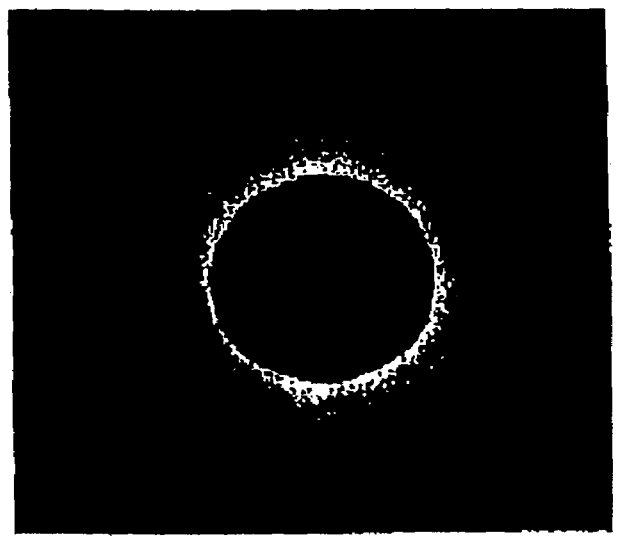
FIG. 14 is an explanatory view showing radial light distribution unevenness generated in the periphery of an illumination area.
Figure 15:
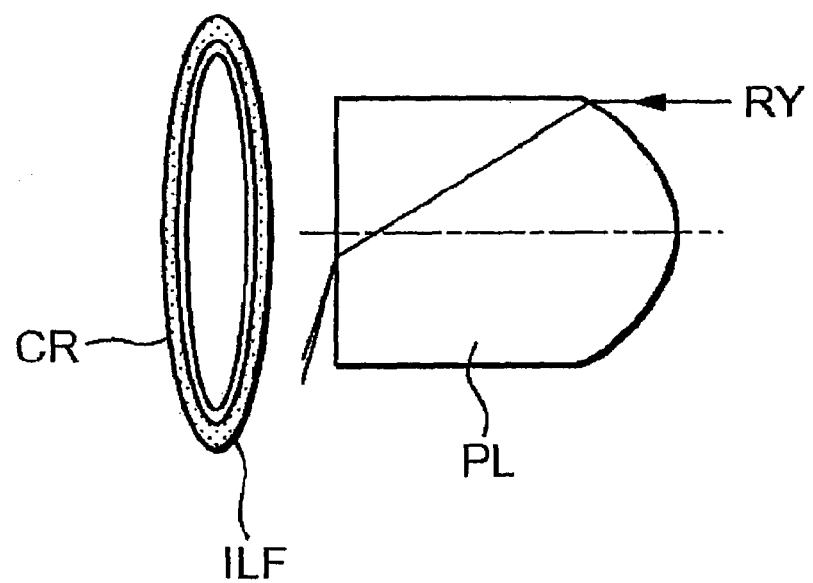
FIG. 15 is an explanatory view showing color unevenness.
Figure 16A:
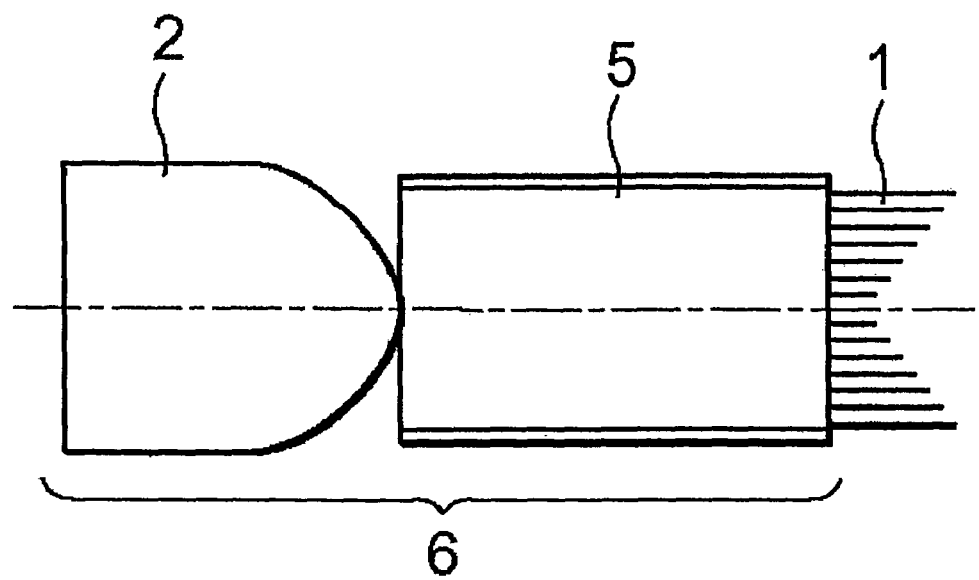
FIGS. 16A and 16B are sectional views along the optical axis, showing a schematic representation of another conventional illumination optical system.
Figure 16B:
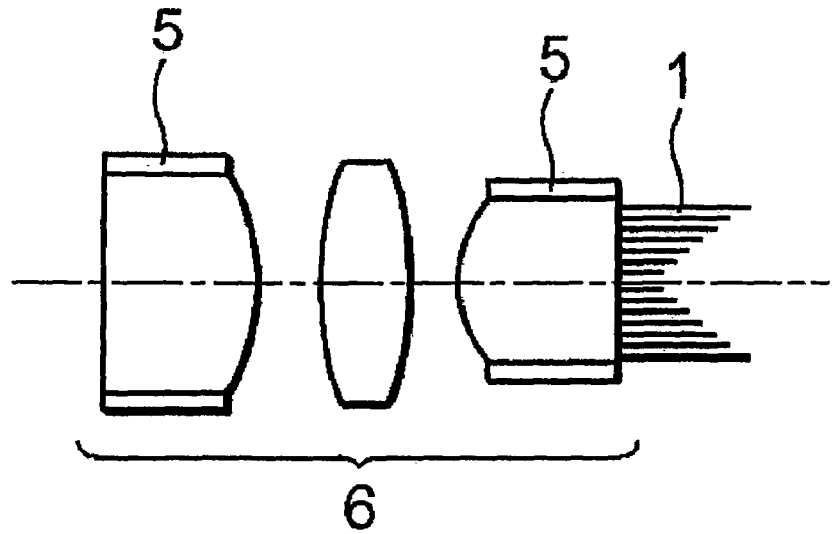
Figure 17:
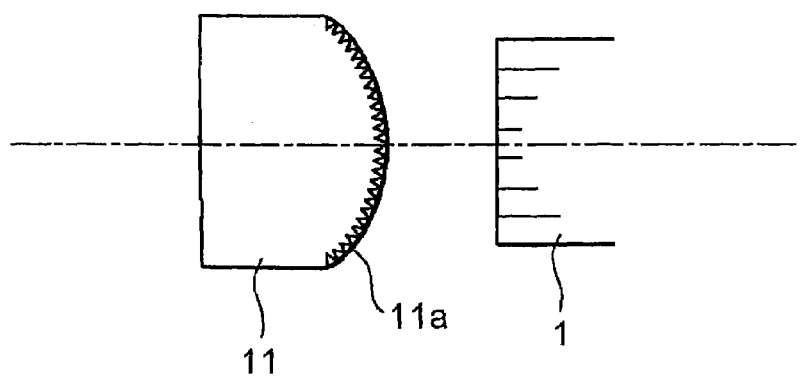
FIG. 17 is a sectional view along the optical axis, showing the schematic representation of still another conventional illumination optical system.
Figure 18A:
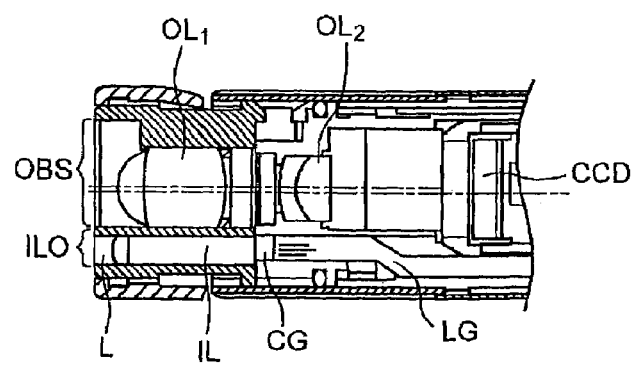
Figure 18B:
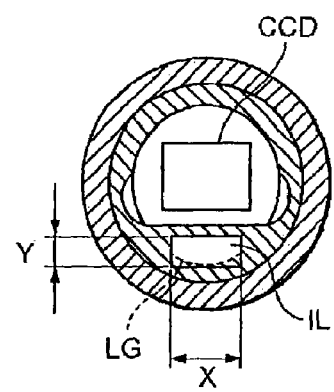

FIG. 12 shows the results of measured MTFs of the illumination lens, and a reference lens using the apparatus of FIG. 11. In this figure, the abscissa indicates a spatial frequency, and the ordinate indicates the MTF (units: %). In FIG. 12, a curve (a) shown by a broken line indicates the MTF of the reference, and a curve (b) shown by a solid line indicates the MTF of the plano-convex lens provided with the roughened surface for use in the illumination optical system. As the evaluated value $\xi$, an MTF at any spatial frequency of 5 to 10 line/mm or an average value of MTFs in the spatial frequency range of 5-10 line/mm may be used. In each embodiment of the present invention, an MTF value evaluated by 7 line/mm is used as the evaluated value $\xi$.

Next, a numerical example of Embodiment 1 will be described. In FIG. 3, $r_1, r_2, \ldots$ denote surface numbers, and $d_1, d_2$ denote surface intervals.

The illumination optical system of Embodiment 1 may be used as the illumination optical system for an endoscope, using only one plano-convex lens 2. The convex surface $r_2$ of the plano-convex lens 2 is formed as a roughened aspherical surface, and light distribution unevenness and color unevenness are prevented from being generated by the roughened surface. The plano-convex lens 2 is disposed in such a manner as to bring the convex surface $r_2$ into contact with an end surface $r_3$ of a light guide fiber bundle 1.

In the illumination optical system of Embodiment 1, the number of lenses is reduced, and costs can be lowered. A total length of the illumination optical system can be shortened, and the length of a hard tip section of the endoscope can also be shortened. Especially in a case where two or more illumination optical systems are tilted and arranged on the tip section of the endoscope in order to illuminate a broad range of an object, an outer diameter of the inserting section can be reduced. Since the roughened surface does not contact the outside of the endoscope, mucus, water, dust or the like does not stick to the roughened surface, and the optical performance is not deteriorated.

The roughened surface of the plano-convex lens 2 is manufactured by the following procedure in Embodiment 1.

First, a reference lens is produced which has the same outer shape as that of the plano-convex lens of Embodiment 1 and in which the convex surface is not a roughened surface but a usual polished surface. The aspherical surface of the plano-convex lens 2 of Embodiment 1 is produced by the process of mold pressing, grinding, and polishing or the like. The roughened surface in the plano-convex lens 2 of Embodiment 1 is produced by working steps including the above-described primary and secondary working, evaluation of the total light quantity ratio using the integrating photometer, and the evaluation of the light distribution unevenness. By the working steps, an illumination optical system for an endoscope can be obtained in which a total light quantity ratio is X=0.80 (L=6.6 lumens, $L_0$=8.3 lumens), and a light distribution unevenness ratio is V=0.43 ($\xi$=13, $\xi_0$=30) when obtained from the two dimensional Fourier transform of an image, and V=0.4 ($\xi$=10, $\xi_0$=25) when obtained from the MTF.

Next, numerical data of the optical member constituting the illumination optical system of Embodiment 1 will be described. It is to be noted that in the numerical data, r denotes a radius of curvature of the optical surface, d denotes a surface interval, Nd denotes a refractive index at a wavelength of d-line, and Vd denotes Abbe's number at the d-line. An aspherical surface Zf(y) is represented by the following equation, assuming that an optical axis direction is Zf, a height from the optical axis is y, and a light travel direction is positive.

$$Zf(y) = \frac{\left(\frac{1}{R}\right)y^2}{1+\sqrt{1-(k+1)\left(\frac{1}{R^2}\right)y^2}} + A_2 y^2 + A_4 y^4 + \ldots + A_n y^n$$

Here, R denotes a radius of curvature of the lens surface, k denotes a conic constant, $A_2$ denotes a 2nd-order aspherical coefficient, $A_4$ denotes a 4th-order aspherical coefficient, and $A_n$ denotes an n-th-order aspherical coefficient. These symbols are common in the following embodiments.

Numerical Data 1 (unit: mm)

| | r | d | Nd | Vd |
|---|---|---|---|---|
| First surface | ∞ | 1.85 | 1.883 | 40.76 |
| Second surface (roughened, aspherical) | −0.675 | 0 | 1 | |
| Third surface (end surface of light guide fiber bundle) | ∞ | | | |

Aspherical coefficient
Second surface: k=−0.625, A4=−4.4671×10$^{-2}$
Maximum outer diameter of plano-convex lens 2: φ1.5
Diameter of light guide fiber bundle 1: φ1.45
Average core interval of light guide fiber bundle 1: 0.06
Optical power Φ1 of plane convex lens 2: 1.309
Maximum sectional area Sx of plane convex lens 2: 1.767 mm$^2$
$\sqrt{Sx} \times \Phi 1$: 1.74

EMBODIMENT 2

Figure 4:
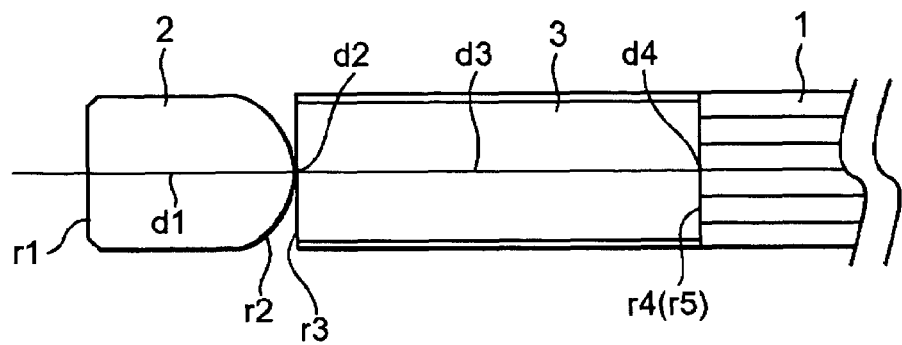
FIG. 4 is a sectional view along the optical axis, showing Embodiment 2 of the present invention.

FIG. 4 is a sectional view along an optical axis, showing the construction of Embodiment 2 of the present invention. In FIG. 4, $r_1$, $r_2$, . . . denote surface numbers, and $d_1$, $d_2$ denote surface intervals.

An illumination optical system of Embodiment 2 comprises a plano-convex lens 2 and a single fiber 3, which together constitute the illumination optical system for an endoscope. A convex surface $r_2$ of the plano-convex lens 2 is formed as a roughened spherical surface, and light distribution unevenness and color unevenness are prevented from being generated by this roughened surface. Additionally, since the single fiber 3 also has a function of reducing the light distribution unevenness, the roughened surface does not have to be as coarse as that formed on the convex aspherical surface $r_2$ of the plano-convex lens 2 of Embodiment 1. Therefore, a light amount loss can be suppressed, and a total quantity of emitted light can be increased. This characteristic of the illumination optical system of Embodiment 2 is effective in a case where a diameter of the endoscope is reduced, accordingly the number of fibers constituting the light guide fiber bundle is reduced.

The plano-convex lens 2 and the single fiber 3 are arranged in such a manner that the end surface $r_4$ of the single fiber 3 is brought into contact with the end surface $r_5$ of the light guide fiber bundle 1, and the end surface $r_3$ of the single fiber 3 is brought into contact with the convex surface $r_2$ of the plano-convex lens 2.

The roughened surface of the plano-convex lens 2 of Embodiment 2 is produced by working steps including the above-described primary and secondary working, evaluation of the total light quantity ratio using the integrating photometer, and the evaluation of the light distribution unevenness in the same manner as in Embodiment 1. By the working steps, an illumination optical system for an endoscope can be obtained in which a total light quantity ratio is X=0.85 (L=6.0 lumens, $L_0$=7.1 lumens), and a light distribution unevenness ratio is V=0.5 ($\xi$=13, $\xi_0$=26) when obtained from the two dimensional Fourier transform of an image, and V=0.5 ($\xi$=20, $\xi_0$=40) when obtained from the MTF. The length of the single fiber 3 needs to be longer than the focal length of the plano-convex lens 2 in order to prevent the generation of light distribution unevenness.

Next, numerical data of the optical members which constitutes the illumination optical system of Embodiment 2 will be shown.

Numerical Data 2 (unit: mm)

| | r | d | Nd | Vd |
|---|---|---|---|---|
| First surface | ∞ | 1.4 | 1.883 | 40.76 |
| Second surface (roughened, spherical) | −0.58 | 0 | 1 | |
| Third surface (end surface of single fiber) | ∞ | 2.7 | 1.80518 | 25.42 |
| Fourth surface | ∞ | 0 | 1 | |
| Fifth surface (end surface of light guide fiber bundle) | ∞ | | | |

Maximum outer diameter of plano-convex lens 2: φ1
Diameter of light guide fiber bundle 1: φ0.95
Average core interval of light guide fiber bundle 1: 0.06
Optical power Φ1 of illumination optical system: 1.522
Maximum sectional area Sx of plano-convex lens 2 and single fiber 3: 0.785 mm$^2$
Length dr of single fiber 3 in optical-axis direction: 2.7
dr×Φ1: 4.11
$\sqrt{Sx} \times \Phi 1$: 1.349
$\sqrt{Sx}/dr$: 0.328

EMBODIMENT 3

Figure 5A:
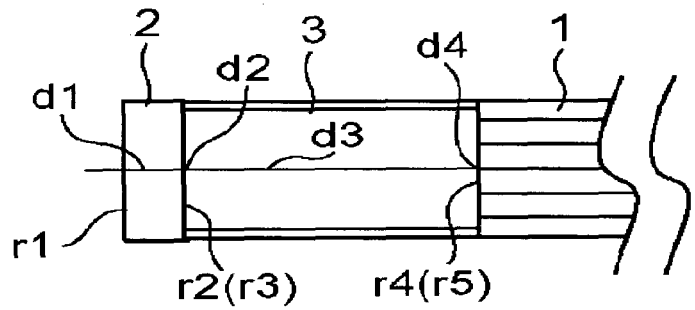
Figure 5B:
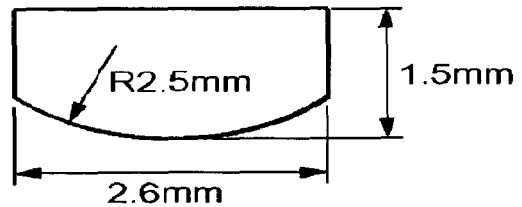

FIG. 5 is an explanatory view showing the construction of Embodiment 3 of the present invention, in which FIG. 5A is a sectional view along an optical axis, and FIG. 5B is a front view of FIG. 5A viewed from the left side. In FIG. 5A, $r_1$, $r_2$, . . . denote surface numbers, and $d_1$, $d_2$ denote surface intervals.

The illumination optical system of Embodiment 3 comprises a plane parallel plate 2 and a single fiber 3, and provides the illumination optical system for an endoscope. A surface $r_2$ is formed as a roughened surface on a light guide fiber bundle 1 side of the plane parallel plate 2. Additionally, outer shapes of the plane parallel plate 2 and the single fiber 3 are not circular, and formed into elongated semicylindrical shapes as shown in FIGS. 5A and 5B.

In an endoscope in which it is difficult to secure an installation space for the illumination optical system, the light guide fiber bundle 1 is disposed in such a manner as to extend along an inner periphery inside a housing, and the outer shape of the light guide fiber bundle is sometimes formed into an elongated semicylindrical shape. On the other hand, much cost is required for working a lens, which has power and which constitutes the illumination optical system into an elongated semicylindrical shape. When the plane parallel plate is used as an optical member forming the illumination optical system, and a section of the plate is formed into a shape other than a circular shape as in the illumination optical system of Embodiment 3, the installation space can be secured at a low cost.

Moreover, the plane parallel plate has the roughened surface in the illumination optical system of Embodiment 3. Therefore, when the section is formed into the shape other than a circular shape, light distribution unevenness can be prevented from being easily generated, and light distribution can be broadened by a diffusion action of the roughened surface.

In formation of the roughened surface of the plane parallel plate 2 in the illumination optical system of Embodiment 3, a reference plane parallel plate is produced which does not have the roughened surface having the same shape as that of Embodiment 3. The roughened surface of the plane parallel plate is produced by working steps including the above-described primary and secondary working, evaluation of the total light quantity ratio using the integrating photometer, and the evaluation of the light distribution unevenness. By the working steps, the illumination optical system for the endoscope can be obtained in which a total light quantity ratio is X=0.73 (L=11.7 lumens, $L_0$=16.0 lumens), and a light distribution unevenness ratio is V=0.35 ($\xi$=7, $\xi_0$=20) when obtained from the two dimensional Fourier transform of an image.

Next, numerical data of the optical members that constitute the illumination optical system of Embodiment 3 will be shown.

Numerical Data 3 (unit: mm)

| | r | d | Nd | Vd |
|---|---|---|---|---|
| First surface | ∞ | 0.4 | 1.883 | 40.76 |
| Second surface (roughened surface) | ∞ | 0 | 1 | |
| Third surface (end surface of single fiber) | ∞ | 2 | 1.80518 | 25.42 |
| Fourth surface | ∞ | 0 | 1 | |
| Fifth surface (end surface of light guide fiber bundle) | ∞ | | | |

Maximum outer shape of plane parallel plate 2: 1.5×2.6
Approximate size of section of light guide fiber bundle 1: 1.5×2.6
Average core interval of light guide fiber bundle 1: 0.08
Optical power $\Phi 1$ of illumination optical system: 0.0
Maximum sectional area Sx of plane parallel plate 2 and single fiber 3: 3.594 mm$^2$
Length dr of single fiber 3 in optical-axis direction: 2
dr×$\Phi 1$: 0.0
$\sqrt{Sx}\times\Phi 1$: 0.0
$\sqrt{Sx}$/dr: 0.948

The above-described embodiments satisfy the major requirement for an illumination optical system, that is to say, the requirement (1) to emit sufficient quantity of light, (2) to have sufficient uniformity of light distribution, and (3) to have a broad range of light distribution. The above-described embodiments also serve to provide an illumination optical system small in diameter, short in length, and with a reduced manufacturing fluctuation at low-cost.

EMBODIMENT 4

Figure 10E:
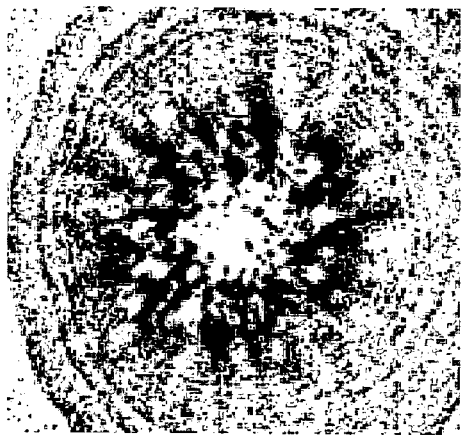
Figure 10F:
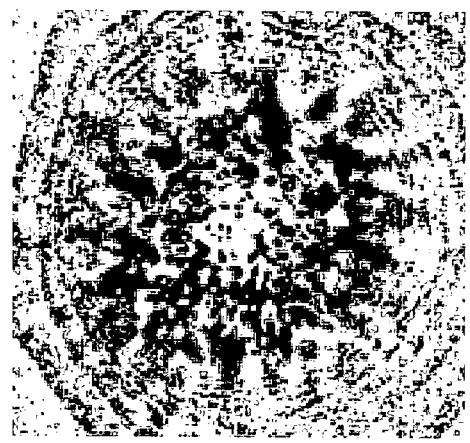

Embodiment 4 has the same structure as Embodiment 2 shown in FIG. 4 and is manufactured in similar process of Embodiment 2. The difference between Embodiments 2 and 4 is that the roughness of the roughened surface formed on the convex surface $r_2$ of the plano-convex surface is finer in Embodiment 4 than in Embodiment 2. This fine roughened surface is formed by extending the working time of the roughened surface using the polishing sheet in the secondary working process. The illumination optical system of Embodiment 4 has a total light quantity ratio of X=0.92 (L=6.5 lumens, $L_0$=7.1 lumens), and a light distribution unevenness ratio is V=0.89 ($\bar{\xi}$=405, $\xi_0$=454) when obtained from a contrast value using the texture analysis of the unevenness-emphasized image. FIGS. 10E shows the unevenness-emphasized image of the plano-convex lens 2 of Embodiment 4, which corresponds to FIG. 10B, and FIG. 10F shows the unevenness-emphasized image of the plano-convex lens of the reference optical system that is formed by replacing the roughened surface of Embodiment 4 with a polished surface. The single fiber 3 is arranged for reducing the light distribution unevenness, the length of which should be longer than the focal length of the plano-convex lens to secure the sufficient effect of reducing the light distribution unevenness.

The numerical date of Embodiment 4 is the same as those of Embodiment 2.

Embodiment 4 provides an illumination optical system for an endoscope that supplies sufficient amount of illumination light and has an excellent light distribution as well as a light distribution unevenness that causes no problem in practical use.

It is to be noted that the single fiber 3 can be omitted. In this case, the light distribution unevenness will slightly increase. However, this type of illumination optical system may be used without any practical problem by restricting the type and uses of the endoscope for which the illumination optical system is applied.

While there has been shown and described what are considered to be exemplary embodiments of the present invention, it will, of course, be understood that various modifications and changes in form or detail could be readily be made without departing from the spirit of the invention. It is, therefore, intended that the invention be not limited to the exact forms described and illustrated, but should be constructed to cover all modifications that may fall within the scope of the appended claims.

What is claimed is:

1. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, and a total quantity of light is $L_0$ emitted by a reference optical system in which all the roughened surfaces of the illumination optical system are replaced with polished surfaces, the illumination optical system satisfies the following condition:

$$0.70 \leq X \leq 0.95,$$

where $X=L/L_0$, wherein the illumination optical system comprises, in order as viewed from an object side, a single lens having a positive power and a single fiber, and wherein assuming that a maximum value of an area of a section of an optical member constituting the illumination optical system is Sx, the section being vertical to an optical axis, and a length of the single fiber in an optical axis direction is dr, the following condition is satisfied:

$$\sqrt{Sx}/dr < 1.$$

2. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, and a total Quantity of light is $L_0$ emitted by a reference optical system in which all the roughened surfaces of the illumination optical system are replaced with polished surfaces, the illumination optical system satisfies the following condition:

$$0.70 \leq X \leq 0.95,$$

where $X=L/L_0$, wherein the total light quantity L of the illumination optical system, and the total light quantity $L_0$ of the reference optical system are evaluated by a measurement method and apparatus based on an integrating photometer method using an integrating photometer, wherein the illumination optical system comprises, in order as viewed from an object side, a single lens having a positive power and a single fiber, and wherein assuming that a maximum value of an area of a section of an optical member constituting the illumination optical system is Sx, the section being vertical to an optical axis, and a length of the single fiber in an optical axis direction is dr, the following condition is satisfied:

$$\sqrt{Sx}/dr < 1.$$

3. An illumination optical system for illuminating an object with light from a light source device comprising a plurality of optical surfaces, at least one of which is formed as a roughened surface and is arranged in a position other than closest to the object, wherein, assuming that an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$$0.30 \leq V \leq 0.70,$$

where $V=\xi/\xi_0$;

wherein the illumination optical system comprises at least one optical member whose outer shape is formed into a shape, which is not circular; and wherein the illumination optical system satisfies the following condition:

$$-2 < \sqrt{Sx} \times \Phi 1 < 2,$$

where Sx denotes a maximum value of an area of a section of an optical member constituting the illumination optical system, vertical to an optical axis, and $\Phi 1$ denotes an optical power of the illumination optical system.

4. An illumination optical system for illuminating an object with light from a light source device comprising a plurality of optical surfaces, at least one of which is formed as a roughened surface and is arranged in a position other than closest to the object, wherein, assuming that an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$$0.30 \leq V \leq 0.70,$$

where $V=\xi/\xi_0$;

wherein the illumination optical system comprises a single lens having a positive power; and wherein the illumination optical system satisfies the following condition:

$$-2 < \sqrt{Sx} \times \Phi 1 < 2,$$

where Sx denotes a maximum value of an area of a section of an optical member constituting the illumination optical system, vertical to an optical axis, and $\Phi 1$ denotes an optical power of the illumination optical system.

5. An illumination optical system for illuminating an object with light from a light source device comprising a plurality of optical surfaces, at least one of which is formed as a roughened surface and is arranged in a position other than closest to the object, wherein, assuming that an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$$0.30 \leq V \leq 0.70,$$

where $V=\xi/\xi_0$;

wherein assuming that a total quantity of light is L emitted to the object by the illumination optical system, and a total quantity of light is $L_0$ emitted by a reference optical system in which all the roughened surfaces of the illumination optical system are replaced with polished surfaces, L and $L_0$ are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which the light distribution image that is subjected to a Fourier transform is used;

wherein the illumination optical system comprises a single lens having a positive power; and wherein the illumination optical system satisfies the following condition:

$$-2 < \sqrt{Sx} \times \Phi1 < 2,$$

where Sx denotes a maximum value of an area of a section of an optical member constituting the illumination optical system, vertical to an optical axis, and $\Phi1$ denotes an optical power of the illumination optical system.

6. An illumination optical system for illuminating an object with light from a light source device comprising a plurality of optical surfaces, at least one of which is formed as a roughened surface and is arranged in a position other than closest to the object, wherein, assuming that an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$$0.30 \leq V \leq 0.70,$$

where $V = \xi/\xi_0$;

wherein assuming that a total quantity of light is L emitted to the object by the illumination optical system, and a total quantity of light is $L_0$ emitted by a reference optical system in which all the roughened surfaces of the illumination optical system are replaced with polished surfaces, L and $L_0$ are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which the MTF is used;

wherein the illumination optical system comprises a single lens having a positive power; and wherein the illumination optical system satisfies the following condition:

$$-2 < \sqrt{Sx} \times \Phi1 < 2,$$

where Sx denotes a maximum value of an area of a section of an optical member constituting the illumination optical system, vertical to an optical axis, and $\Phi1$ denotes an optical power of the illumination optical system.

7. The illumination optical system according to claim 5, satisfying the following conditions:

$$0.78 \leq X \leq 0.92; \text{ and}$$

$$0.35 \leq V \leq 0.60;$$

where $X = L/L_0$.

8. The illumination optical system according to claim 6, satisfying the following conditions:

$$0.78 \leq X \leq 0.92; \text{ and}$$

$$0.35 \leq X \leq 0.60;$$

where $X = L/L_0$.

9. The illumination optical system according to claim 4, wherein assuming that a total quantity of light is L emitted to the object by the illumination optical system, and a total quantity of light is $L_0$ emitted by a reference optical system in which all the roughened surfaces of the illumination optical system are replaced with polished surfaces, the illumination optical system satisfies the following conditions:

$$0.78 \leq X \leq 0.92; \text{ and}$$

$$0.35 \leq V \leq 0.60,$$

where $X = L/L_0$.

10. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$$0.85 \leq X < 1.00$$

$$0.60 \leq V \leq 0.95,$$

where $X = L/L_0$ and $V = \xi/\xi_0$;

wherein the total light quantity L of the illumination optical system, and the total light quantity $L_0$ of the reference optical system are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which a contrast value obtained by a texture analysis of an image of the light distribution unevenness is used;

wherein the illumination optical system comprises, in order as viewed from an object side, a single lens having a positive power and a single fiber, and wherein assuming that a maximum value of an area of a section of an optical member constituting the illumination optical system is Sx, the section being vertical to an optical axis, and a length of the single fiber in an optical axis direction is dr, the following condition is satisfied:

$$\sqrt{Sx}/dr < 1.$$

11. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$0.85 \leq X < 1.00$ $0.60 \leq V \leq 0.95$, where $X = L/L_0$ and $V = \xi/\xi_0$;

wherein the total light quantity L of the illumination optical system, and the total light quantity $L_0$ of the reference optical system are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which the light distribution image that is subjected to a Fourier transform is used;

wherein the illumination optical system comprises, in order as viewed from an object side, a single lens having a positive power and a single fiber, and wherein assuming that a maximum value of an area of a section of an optical member constituting the illumination optical system is Sx, the section being vertical to an optical axis, and a length of the single fiber in an optical axis direction is dr, the following condition is satisfied:

$\sqrt{Sx}/dr < 1$.

12. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$0.85 \leq X < 1.00$ $0.60 \leq V \leq 0.95$, where $X = L/L_0$ and $V = \xi/\xi_0$;

wherein the total light quantity L of the illumination optical system, and the total light quantity $L_0$ of the reference optical system are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which the MTF is used;

wherein the illumination optical system comprises, in order as viewed from an object side, a single lens having a positive power and a single fiber, and wherein assuming that a maximum value of an area of a section of an optical member constituting the illumination optical system is Sx, the section being vertical to an optical axis, and a length of the single fiber in an optical axis direction is dr, the following condition is satisfied:

$\sqrt{Sx}/dr < 1$.

13. An illumination optical system for illuminating an object with light from a light source device comprising a plurality of optical surfaces, at least one of which is formed as a roughened surface and is arranged in a position other than closest to the object, wherein, assuming that an evaluated value of light distribution unevenness is $\xi$ projected to the object by the illumination optical system, and an evaluated value of light distribution unevenness is $\xi_0$ projected by a reference optical system in which all the roughened surfaces of the illumination optical system are replaced with polished surfaces, the illumination optical system satisfies the following condition:

$0.30 \leq V \leq 0.70$, where $V = \xi/\xi_0$;

wherein assuming that a total quantity of light is L emitted to the object by the illumination optical system, and a total quantity of light is $L_0$ emitted by a reference optical system in which all the roughened surfaces of the illumination optical system are replaced with polished surfaces, L and $L_0$ are evaluated by a measurement method and apparatus based on an integrating photometer method using an integrating photometer;

wherein the evaluated value $\xi$ of the light distribution unevenness of the illumination optical system, and the evaluated value $\xi_0$ of the light distribution unevenness of the reference optical system are evaluated by a measurement method and apparatus in which a contrast value obtained by a texture analysis of an image of the light distribution unevenness is used;

wherein the illumination optical system comprises a single lens having a positive power; and wherein the illumination optical system satisfies the following condition:

$-2 < \sqrt{Sx} \times \Phi 1 < 2$, where Sx denotes a maximum value of an area of a section of an optical member constituting the illumination optical system, vertical to an optical axis, and $\Phi 1$ denotes an optical power of the illumination optical system.

14. An illumination optical system for illuminating an object with light from a light source device comprising a plurality of optical surfaces, at least one of which is formed as a roughened surface and is arranged in a position other than closest to the object, wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is ξ projected to the object by the illumination optical system, and an evaluated value of light distribution unevenness is $ξ_0$ projected by a reference optical system in which all the roughened surfaces of the illumination optical system are replaced with polished surfaces, the illumination optical system satisfies the following condition:

$0.85 \leq X < 1.00$ $0.60 \leq V \leq 0.95$, where $X = L/L_0$ and $V = ξ/ξ_0$;
wherein the total light quantity L of the illumination optical system, and the total light quantity $L_0$ of the reference optical system are evaluated by a measurement method and apparatus based on an integrating photometer method using an integrating photometer;
wherein the evaluated value ξ of the light distribution unevenness of the illumination optical system, and the evaluated value $ξ_0$ of the light distribution unevenness of the reference optical system are evaluated by a measurement method and apparatus in which a contrast value obtained by a texture analysis of an image of the light distribution unevenness is used;
wherein the illumination optical system comprises a single lens having a positive power; and
wherein the illumination optical system satisfies the following condition:

$×2 < \sqrt{Sx} × Φ1 < 2$, where Sx denotes a maximum value of an area of a section of an optical member constituting the illumination optical system, vertical to an optical axis, and Φ1 denotes an optical power of the illumination optical system.

15. An illumination optical system for illuminating an object with light from a light source device comprising a plurality of optical surfaces, at least one of which is formed as a roughened surface and is arranged in a position other than closest to the object,
wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is ξ projected to the object by the illumination optical system, and an evaluated value of light distribution unevenness is $ξ_0$ projected by a reference optical system in which all the roughened surfaces of the illumination optical system are replaced with polished surfaces, the illumination optical system satisfies the following condition:

$0.85 \leq X < 1.00$ $0.60 \leq V \leq 0.95$, where $X = L/L_0$ and $V = ξ/ξ_0$;
wherein the total light quantity L of the illumination optical system, and the total light quantity $L_0$ of the reference optical system are evaluated by a measurement method and apparatus based on an integrating photometer method using an integrating photometer;
wherein the evaluated value ξ of the light distribution unevenness of the illumination optical system, and the evaluated value $ξ_0$ of the light distribution unevenness of the reference optical system are evaluated by a measurement method and apparatus in which the light distribution image that is subjected to a Fourier transform is used;
wherein the illumination optical system comprises a single lens having a positive power; and
wherein the illumination optical system satisfies the following condition:

$-2 < \sqrt{Sx} × Φ1 < 2$, where Sx denotes a maximum value of an area of a section of an optical member constituting the illumination optical system, vertical to an optical axis, and Φ1 denotes an optical power of the illumination optical system.

16. An illumination optical system for illuminating an object with light from a light source device comprising a plurality of optical surfaces, at least one of which is formed as a roughened surface and is arranged in a position other than closest to the object,
wherein, assuming that a total quantity of light emitted to the object by the illumination optical system is L, a total quantity of light is $L_0$ emitted by a reference optical system in which all the roughened surfaces of the illumination optical system are replaced with polished surfaces, an evaluated value of light distribution unevenness is ξ projected to the object by the illumination optical system, and an evaluated value of light distribution unevenness is $ξ_0$ projected by a reference optical system in which all the roughened surfaces of the illumination optical system are replaced with polished surfaces, the illumination optical system satisfies the following condition:

$0.85 \leq X < 1.00$ $0.60 \leq V \leq 0.95$, where $X = L/L_0$ and $V = ξ/ξ_0$;
wherein the total light quantity L of the illumination optical system, and the total light quantity $L_0$ of the reference optical system are evaluated by a measurement method and apparatus based on an integrating photometer method using an integrating photometer;
wherein the evaluated value ξ of the light distribution unevenness of the illumination optical system, and the evaluated value $ξ_0$ of the light distribution unevenness of the reference optical system are evaluated by a measurement method and apparatus in which the MTF is used;
wherein the illumination optical system comprises a single lens having a positive power; and
wherein the illumination optical system satisfies the following condition:

$-2 < \sqrt{Sx} × Φ1 < 2$, where Sx denotes a maximum value of an area of a section of an optical member constituting the illumination optical system, vertical to an optical axis, and Φ1 denotes an optical power of the illumination optical system.

* * * * *